(12) United States Patent
Miller et al.

(10) Patent No.: US 11,883,322 B1
(45) Date of Patent: Jan. 30, 2024

(54) SIMULTANEOUS THERMAL AND COOLING THERAPEUTIC DEVICE HAVING A REMOVABLE FLEXIBLE RECEPTACLE

(71) Applicants: Wayne Allan Miller, Land O' Lakes, FL (US); Bruce Wayne Miller, Naples, FL (US)

(72) Inventors: Wayne Allan Miller, Land O' Lakes, FL (US); Bruce Wayne Miller, Naples, FL (US)

( * ) Notice: Subject to any disclaimer, the term of this patent is extended or adjusted under 35 U.S.C. 154(b) by 0 days.

(21) Appl. No.: 18/181,726

(22) Filed: Mar. 10, 2023

(51) Int. Cl.
*A61F 7/02* (2006.01)

(52) U.S. Cl.
CPC ........ *A61F 7/02* (2013.01); *A61F 2007/0268* (2013.01); *A61F 2007/0285* (2013.01)

(58) Field of Classification Search
CPC ................ A61F 7/02; A61F 2007/0268; A61F 2007/0285; A61F 2007/0217; A61F 2007/0219; A61F 2007/022; A61F 2007/0271
See application file for complete search history.

(56) References Cited

U.S. PATENT DOCUMENTS

| | | | | |
|---|---|---|---|---|
| 11,154,419 | B2* | 10/2021 | Miller | A61F 7/02 |
| 2007/0021810 | A1* | 1/2007 | Paulin | A61F 7/02 |
| | | | | 607/114 |
| 2012/0065259 | A1* | 3/2012 | Zhang | A61K 31/245 |
| | | | | 514/537 |
| 2014/0188199 | A1* | 7/2014 | Enderby | A61M 1/062 |
| | | | | 607/108 |
| 2017/0360602 | A1* | 12/2017 | Nishioka | A61F 7/03 |
| 2020/0405533 | A1* | 12/2020 | Check | A61F 7/10 |
| 2022/0264971 | A1* | 8/2022 | DeLara | A41D 13/1245 |

* cited by examiner

*Primary Examiner* — Gary Jackson
*Assistant Examiner* — Sebastian X Lukjan
(74) *Attorney, Agent, or Firm* — Tiffany C. Miller; Inventions International Inc.

(57) ABSTRACT

A therapeutic device having a first removable pack having a first temperature, a second removable pack having a second temperature, a flexible receptacle having a first compartment and a pocket. The first compartment of the flexible receptacle is configured to receive the first removable pack. The pocket is connected to the outer wall surface of the flexible receptacle and forms a second compartment configured to receive the second removable pack through a first opening of the pocket. The therapeutic device combines both hot and cold therapy to work simultaneously together. The application of both hot and cold to the site of an injury of a user stimulates blood circulation to an injured muscle with heat and reduces inflammation with cold to facilitate a faster and more efficient recovery process of the afflicted area.

6 Claims, 6 Drawing Sheets

SIMULTANEOUS THERMAL AND COOLING THERAPEUTIC DEVICE HAVING A REMOVABLE FLEXIBLE RECEPTACLE

BACKGROUND OF THE INVENTION

1. Field of the Invention

This invention relates, generally, to a removable flexible receptacle for a simultaneous thermal and cooling therapeutic device. More particularly, it relates to a flexible receptacle apparatus having a first compartment retaining a removable cold pack and a second compartment retaining a removable hot pack.

2. Background Art

This novel therapeutic device is configured to help injuries associated with including, but not limited to, sore muscles, sprained muscles, or pulled muscles. The therapeutic device when applied to the injury reduces inflammation with ice or cold packs while also stimulating circulation in the area with hot packs, simultaneously. Many therapeutic devices in today's market either use hot or cold to help with symptoms associated with injury. However, these therapeutic devices do not use both hot and cold at the same time. Using hot and cold together can result in a faster and more efficient way to reduce inflammation, therefore reducing the amount of therapy or product needed to alleviate the pain of the area. Thus, there is a need for a therapeutic device that combines the use of hot and cold in a single therapeutic device in an attempt to save time and energy, to provide more comfort to a user, and to more effectively reduce injury mediated inflammation.

Currently, when an individual has a muscle injury, they use either ice alone or heat alone to treat it. In an example of a muscle injury treatment method, contrast therapy is the application of heat for approximately 20 minutes followed by an application of cold such as a cold pack or ice for approximately 20 minutes. There is a need for a novel therapeutic device configured to combine a cold and hot pack together to deliver simultaneous hot and cold therapy to a user. As a result, the novel therapeutic device is configured to reduce inflammation and stimulate more blood flow to the injured or swollen area. The sensation a user experiences from using a combined hot and cold therapeutic device relaxes the nerves associated with the brain's response to injury. For example, by using hot and cold at the same time, the signals of the brain become confused and may alleviate the area of injury quicker.

In another example of a muscle injury treatment method, cold therapy is effective for pain and inflammation reduction. Cold cools the skin tissue which results in narrowing of blood vessels in a process vasoconstriction. Vasoconstriction reduces swelling, reduces inflammation, and reduces muscle spasms of the injured area. There is a need to take a standard cold pack and combine it together with a hot pack, resulting in a contrast therapy that works at the same time.

In another example of a muscle injury treatment method, heat therapy effectively increases tissue extensibility and improves muscle movement after an injury. Heat therapy also induces vasodilation which draws blood into targeted tissues and increases blood flow. This increase in blood flow is beneficial because the blood flow delivers required oxygen and nutrients to the injured area as well as removes cellular waste. The warmth of heat therapy is associated with a decrease in muscle spasms, relaxes tense muscles, relieves pain, and may increase the range in motion. Heat therapy also stimulates the sensory receptors in the skin, resulting in a decrease in transmission of pain signals to the brain in an attempt to relieve discomfort during an injury. Thus, heat therapy promotes healing of the muscles and joints. There is a need to take a standard hot pack and combine it together with a cold pack, resulting in a contrast therapy that works at the same time.

However, in view of the prior art considered as a whole at the time the present invention was made, it was not obvious to those of ordinary skill in the pertinent art how the identified needs could be fulfilled.

SUMMARY OF THE INVENTION

The long-standing but heretofore unfulfilled need for a therapeutic device having a first removable pack having a first temperature, a second removable pack having a second temperature, a flexible receptacle having a first compartment and a pocket. The first compartment of the flexible receptacle is configured to receive the first removable pack. The pocket is connected to the outer wall surface of the flexible receptacle and forms a second compartment configured to receive the second removable pack through a first opening of the pocket. The therapeutic device combines both hot and cold therapy to work simultaneously together. The application of both hot and cold to the site of an injury of a user stimulates blood circulation to an injured muscle with heat and reduces inflammation with cold to facilitate a faster and more efficient recovery process of the afflicted area. The application of both hot and cold to the site of an injury of a user stimulates blood circulation to an injured muscle with heat and reduces inflammation with cold to facilitate a faster and more efficient recovery process of the afflicted area and is now met by a new, useful, and non-obvious invention.

The following description and drawings are illustrative and are not to be construed as limiting. Numerous specific details are described to provide a thorough understanding. However, in certain instances, well known or conventional details are not described in order to avoid obscuring the description. References to one or an embodiment in the present disclosure are not necessarily references to the same embodiment; and, such references refer to at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

In an alternate embodiment, the standard hot packs and cold packs can be combined together with a flexible receptacle, including, but not limited to, a flexible receptacle, a pouch, a flexible receptacle having a pocket, and/or a flexible receptacle having a pocket with a window configured to expose at least a portion of a pack being retained within the pocket.

In a preferred embodiment, the flexible receptacle has a main compartment configured to receive a standard hot or cold pack. It is within the scope of this invention for the flexible receptacle to be made of any material including, but not limited to, terrycloth fabric, microfiber, waffle fabric, 100% cotton, a highly elastic synthetic fabric, and/or made from a variety of fibers such as elastane. The flexible receptacle has a pocket connected thereto. The pocket may be centrally located on the flexible receptacle. The pocket is configured to receive and retain a standard hot or cold pack. This therapeutic device can then be placed on the injury and both the heat and cold will work together to stimulate blood flow and reduce inflammation to the afflicted area. It is within the scope of this invention for the novel therapeutic device to have a flexible receptacle being any shape and/or size including, but not limited to, a donut shape, rounded, oval, square, or rectangular.

In an alternate embodiment, the novel therapeutic device the exterior flexible receptacle has a pocket connected thereto. The pocket and/or flexible receptacle may be made of a thermal material having a metallic layer. It is within the scope of this invention for the thermal material to be thermal batting, thermal fabric, thermal interfacing, and/or a combination of thermal batting, thermal fabric, and thermal interfacing. It is within the scope of this invention for thermal batting to have insulting properties. Thermal batting is made with hollow, polyester fibers that have been needle-punched through a non-woven substrate and then through a reflective metalized poly film. The hollow fibers insulate by resisting conduction while the metalized poly film reflects radiant energy back to the hot and/or cold pack. The thermal fabric may withstand high temperatures without scorching. The thermal interfacing is a light weight insulating material. In another example of thermal batting, the combination of the reflective material and insulating polyester batting forms a barrier to moisture for the flexible receptacle. Thermal fabric may be made of 100% aluminum with a 100% cotton backing, which does not have any insulating properties, it can protect from heat.

The novel simultaneous thermal and cooling therapeutic device has a flexible receptacle with a pocket having a window configured to receive and retain a novel hot or cold pack having at least a portion of the hot or cold pack being exposed when inserted into the pocket. It is within the scope of this invention for the removable second pack to be a vessel retaining including, but not limited to, a refrigerant gel, ice, freezable gel, water, or beads. The vessel is a container, a pouch, a pack capable of retaining the material to be cooled to the second cooler temperature. It is also within the scope of this invention for the cold pack to be made from a flexible soft plastic material on the outside that retains the substance or material configured to be cooled to a second temperature.

It is within the scope of this current invention for the removable cold pack to be reusable or an instant cold pack.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Figure 1:
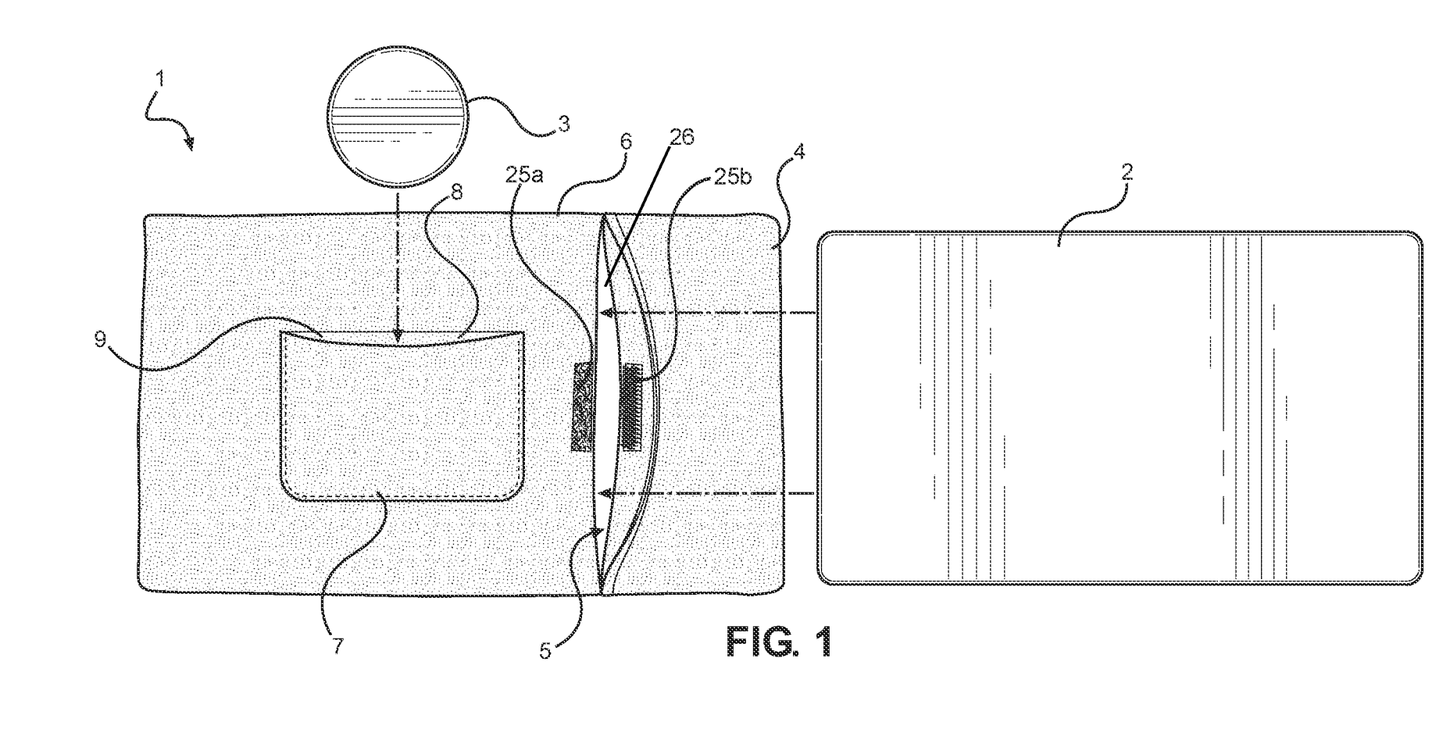
FIG. 1 is a front exploded view of the novel therapeutic device with a flexible receptacle having a first compartment configured to receive and retain first standard removable pack, the flexible receptacle having a pocket configured to receive a second standard removable pack.
Figure 2:
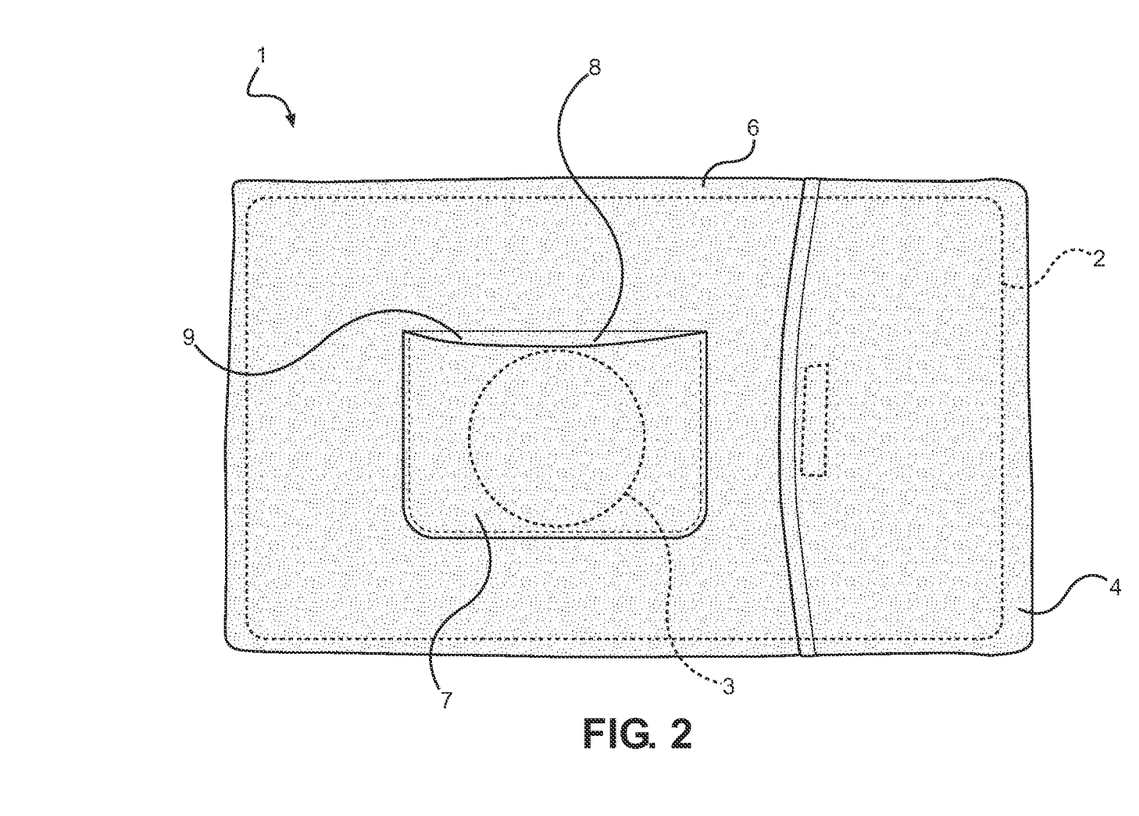
FIG. 2 is a front view of the novel therapeutic device with a first standard removable pack retained within a first compartment of the flexible receptacle, a second standard removable pack is retained within a pocket of the flexible receptacle.

FIGS. 1 and 2 illustrate novel simultaneous thermal and cooling therapeutic device 1 having first removable pack 2 has a first temperature. First removable pack 2 may be a standard hot or a standard cold pack. It is within the scope of this invention for standard to include, but not be limited to, already existing, store bought, any hot or cold pack. Second removable pack 3 has a second temperature. It is within the scope of this invention for the first and second temperatures to be the same, substantially the same or different. For example, first removable pack 2 may be a hot pack while second removable pack 3 may be a cold pack. In another example, first removable pack 2 may be a hot pack while second removable pack 3 may be a hot pack. In another example, first removable pack 2 may be a cold pack while second removable pack 3 may be a cold pack.

FIG. 1 illustrates flexible receptacle 4 having first compartment 5. Flexible receptacle 4 has opening 26 bordering first compartment 5. A fastener may be used to close opening 26 of first compartment 5. It is within the scope of this invention for fastener 25 to include, but not be limited to, a zipper, a clasp, a button, and/or a first portion 25a of a hook and loop fastener configured to connect with a second portion 26a of a hook and loop fastener. It is within the scope of this invention for flexible receptacle 4 to be a case, a sack, a pouch, a bag, or a sleeve. Referring now to FIGS. 1 and 2, flexible receptacle 4 having outer wall surface 6. First compartment 5 (FIG. 1) of flexible receptacle 4 is configured to receive first removable pack 2. Pocket 7 is connected to outer wall surface 6 of flexible receptacle 4. Pocket 7 has opening 9 bordering second compartment 8 of flexible receptacle 4. Second compartment 8 of flexible receptacle 4 is configured to receive second removable pack 3 through first opening 9 of pocket 7.

Figure 3:
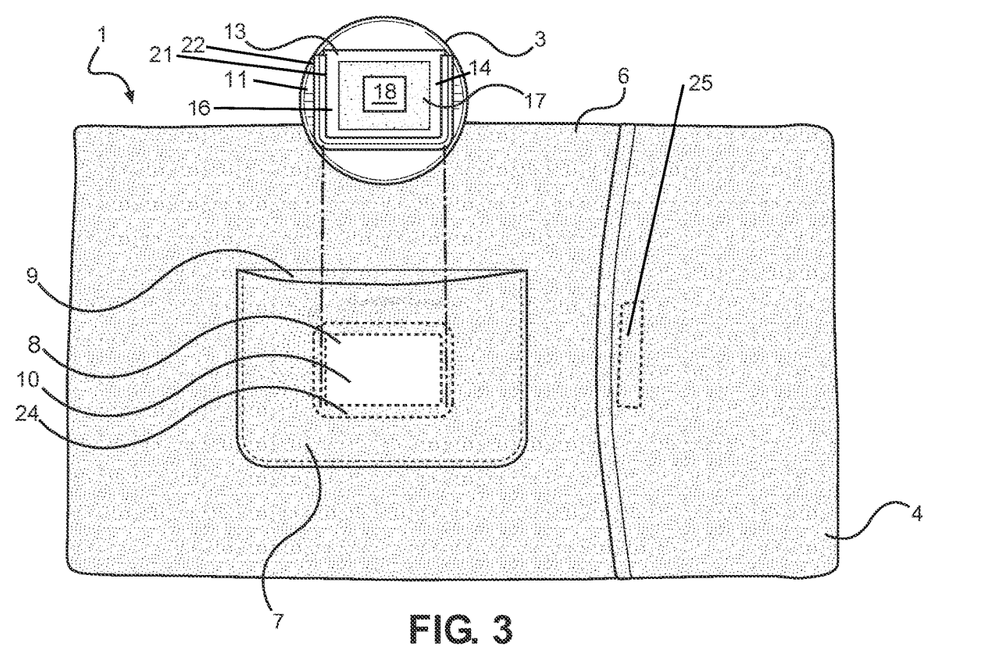
FIG. 3 is a front exploded view of an alternate embodiment of the novel therapeutic device with a flexible receptacle having a pocket with a window and having an uninstalled novel removable second pack, the window of the pocket having a magnetic frame, the pocket is configured to receive a novel removable second pack with a magnetic retaining structure retaining a removable layer of material having at least one substance, the substance portion of the layer of material is configured to be accessible through the window of the pocket when the novel removable second pack is retained in the pocket, the magnetic retaining structure of the removable second pack is configured to be magnetically connected to the magnetic frame of the window of the pocket when installed.
Figure 4:
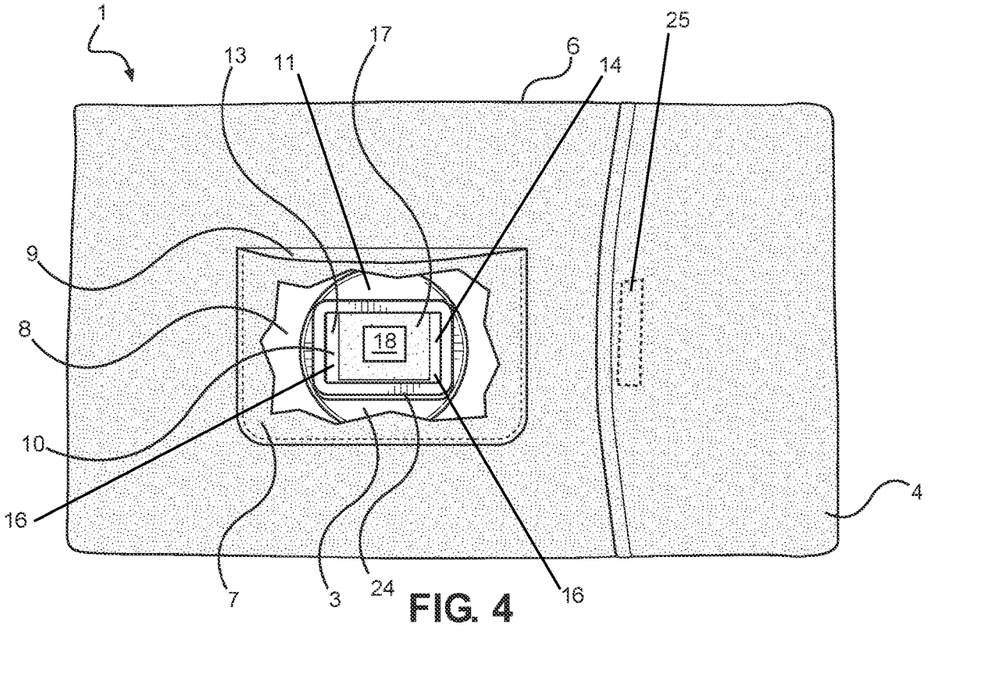
FIG. 4 is a front cut-away view of an alternate embodiment of the novel therapeutic device with a flexible receptacle having a pocket with a window and having an installed novel removable second pack, the window of the pocket having a magnetic frame, the pocket retains a novel removable second pack with a magnetic retaining structure retaining a removable layer of material having at least one substance, the substance portion of the layer of material is accessible through the window of the pocket when the novel removable second pack is retained in the pocket, the magnetic retaining structure of the removable second pack is magnetically connected to the magnetic frame of the window of the pocket when installed.
Figure 5:
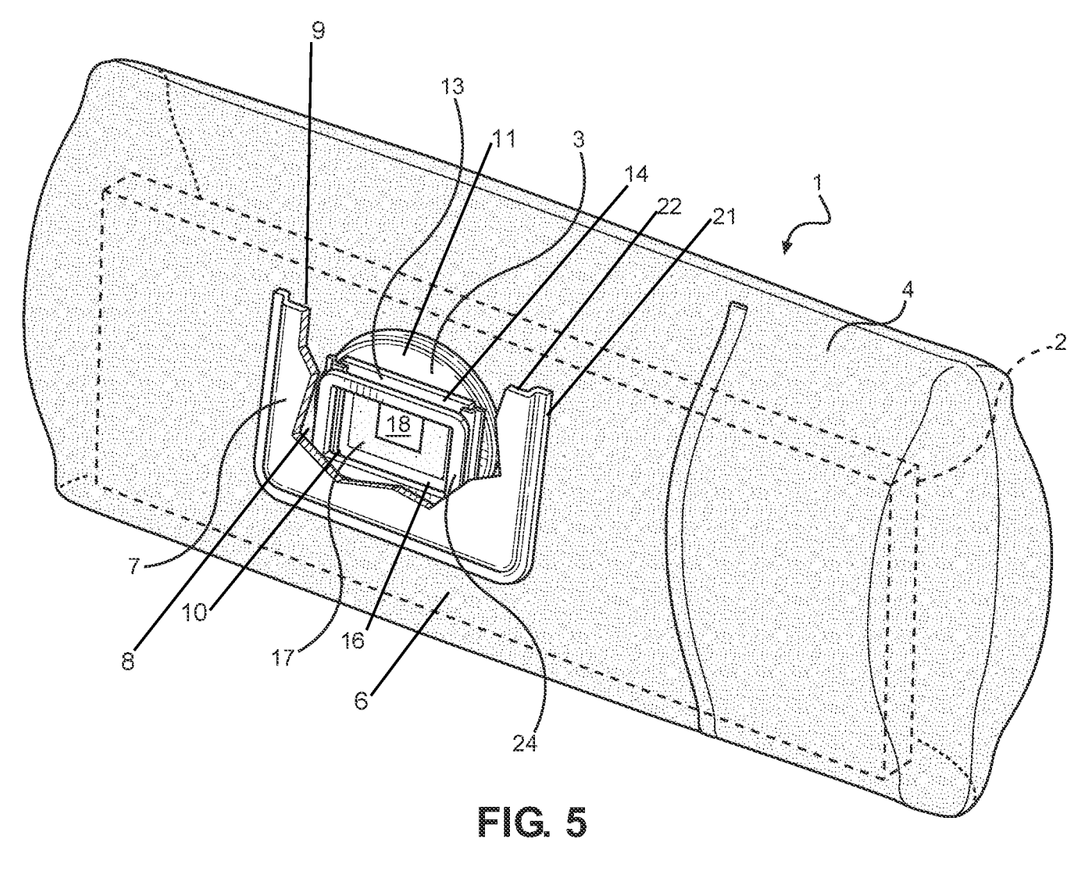
FIG. 5 is a perspective front cut-away view of an alternate embodiment of the novel therapeutic device with a flexible receptacle having a pocket with a window and having an installed novel removable second pack, the window of the pocket having a magnetic frame, the pocket retains a novel removable second pack with a magnetic retaining structure retaining a removable layer of material having at least one substance, the substance portion of the layer of material is accessible through the window of the pocket when the novel removable second pack is retained in the pocket, the magnetic retaining structure of the removable second pack is magnetically connected to the magnetic frame of the window of the pocket when installed.

FIGS. 3-5 show an alternate embodiment of novel simultaneous thermal and cooling therapeutic device 1 of FIGS. 1 and 2 where flexible receptacle 4 has pocket 7 with a second opening forming window 10. Flexible receptacle 4 has outer wall surface 6. Pocket 7 is connected to outer wall surface 6 of flexible receptacle 4. Pocket 7 has opening 9 bordering second compartment 8 of flexible receptacle 4. Second compartment 8 of flexible receptacle 4 is configured to receive second removable pack 3 through first opening 9 of pocket 7. It is within the scope of this invention for pocket 7 of FIGS. 1-5 to be made of a thermal material. Pocket 7 may have an opening forming window 10. FIG. 5 shows first pack 2 being retained within flexible receptacle 4 with second pack 3 positioned within pocket 7. FIGS. 3 and 4 illustrate fastener 25 configured to maintain a closed orientation of the first compartment opening of flexible receptacle 4. Simultaneous thermal and cooling therapeutic device 1 has window 10 which is formed from an opening in a surface of pocket 7. Magnetic frame 24 borders the perimeter of window 10. It is within the scope of this invention for magnetic frame to be a magnet, a magnetic object, and/or any magnetic material capable of producing a magnetic field.

Figure 6:
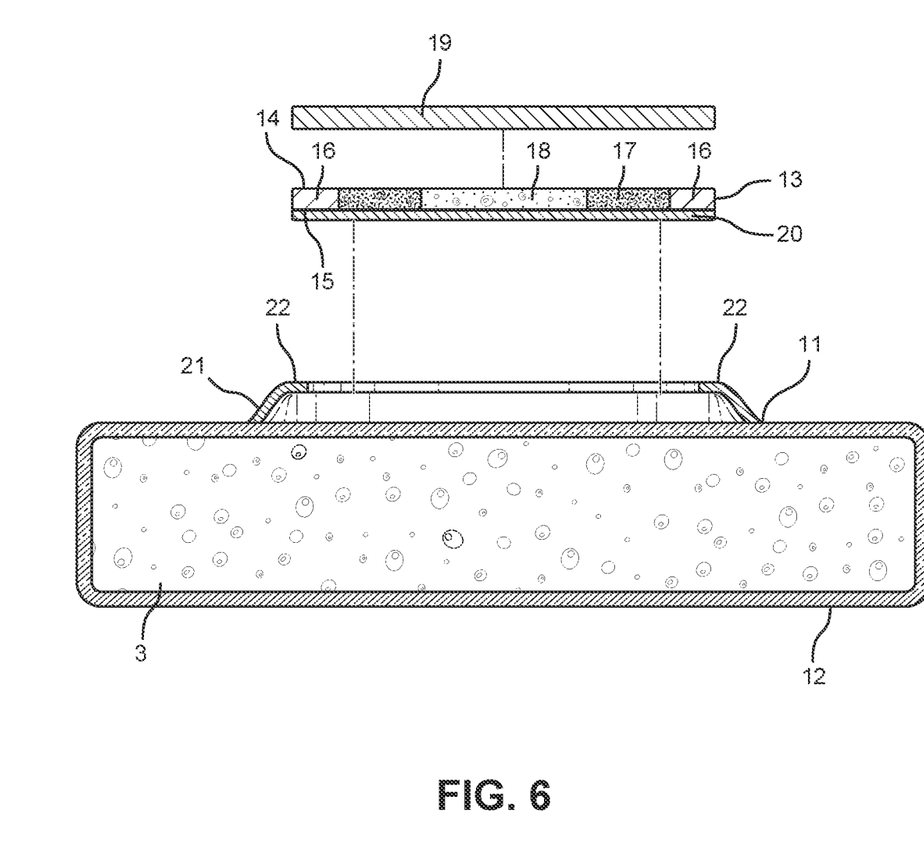
FIG. 6 is a side perspective view of an alternate embodiment of the novel removable second pack with a retaining structure receiving a removable layer of material having at least one substance.
Figure 7:
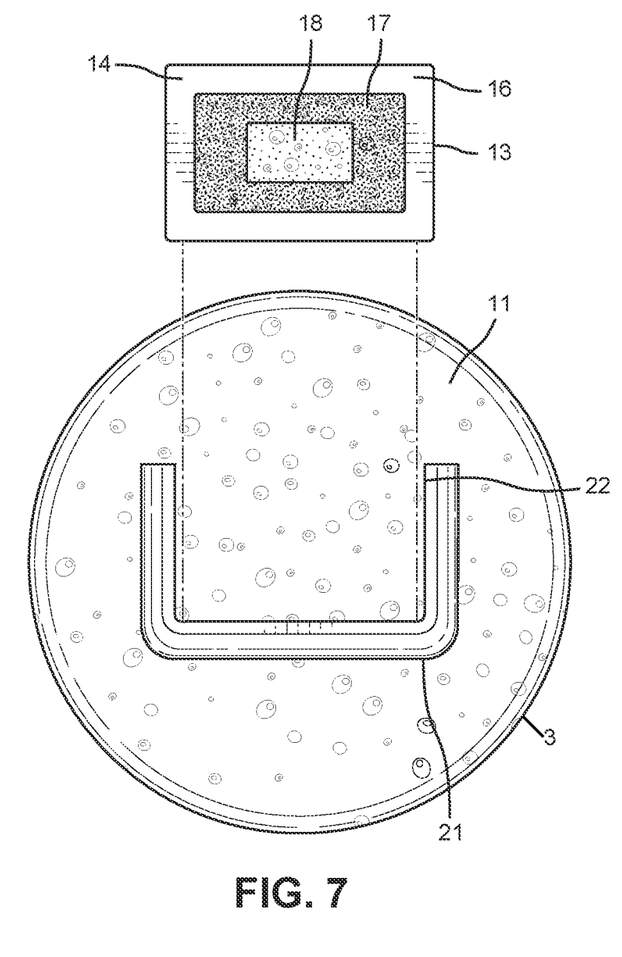
FIG. 7 is a top exploded view of the alternate embodiment of the novel removable second pack with a retaining structure receiving a removable layer of material having at least one substance; and, FIG. 8 is a perspective view of the alternate embodiment of the novel removable second pack with a retaining structure receiving a removable layer of material having at least one substance.
Figure 8:
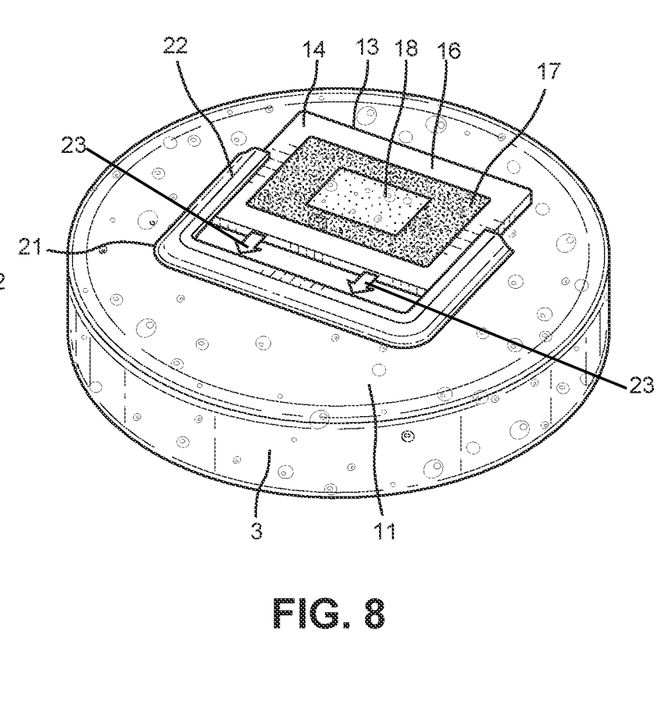

Referring now to FIGS. 3-8 removable second pack 3 has first side 11 located opposite second side 12 (FIG. 6). FIG. 6 best illustrates layer of material 13 having first side 14 located opposite second side 15. Layer of material 13 is removably connected to first side 11 of removable second pack 3. FIGS. 3-5 best show first side 14 of layer of material 13 having substance-free outer perimeter 16. It is within the scope of this invention for substance-free outer perimeter 16 to be made of a magnetic material configured to magnetically connect layer of material 16 to magnetic window frame 24 of pocket 7. Layer of material 13 has first substance 17 having an outer perimeter edge located in close proximity to second substance 18 having an outer perimeter edge. First substance 17 borders outer perimeter edge of second substance 18. The outer perimeter edge of first substance 17 borders substance-free outer perimeter 16 of layer of material 13.

Referring again to FIGS. 3-8, first side 11 of removable second pack 3 has retaining structure 21 configured to retain at least a portion of layer of material 13. FIGS. 3, 5-8 best illustrate retaining structure 21 having a U-shaped wall having flange 22. Flange 22 is overlaying at least a portion of substance-free outer perimeter 16 of layer of material 13. FIGS. 3 and 5 best illustrate first substance 17 and second substance 18 are in alignment with window 10 of pocket 7 of flexible receptacle 4 when flange 22 of retaining structure 21 of second pack 3 is connected to substance-free outer perimeter 16 of layer of material 13 when layer of material 13 is inserted 23 (FIG. 8) into retaining structure 21 and when second pack 3 is retained in pocket 7 of flexible receptacle 4. It is within the scope of this invention for flange 22 and or retaining structure 21 of removable second pack 3 to be made of a magnetic material. Flange 22 is configured to overlay at least a portion of substance-free outer perimeter 16 of layer of material 13. First substance 17 and second substance 18 are in alignment with said second opening of said pocket of said flexible receptacle when said flange is connected to said substance-free outer perimeter of said layer of material, said flange of said retaining structure of said removable second pack is magnetically connected to said pocket of said flexible receptacle.

FIG. 6 depicts second pack 3 configured to be in communication with layer of material 13. First side 14 of layer of material 14 includes any material such as an insert, a patch, a disc, or a pad that may be saturated with and/or may retain at least one substance 17, 18. It is within the scope of this invention for substance 17, 18 to include but not be limited to, any medication, oil, cream, or combination of the aforementioned. Layer of material 13 has first side 14 located opposite second side 15. First side 14 of layer of material 13 can have barrier member 19. Barrier member 19 is any material including, but not limited to, wax paper, paper, plastic, a sticker, foil, or cardboard that may overlay substance 17, 18. Barrier member 19 serves the purpose of overlaying and covering substance 17, 18 so these substances do not evaporate, become dried out, become contaminated, or become exposed when not in use. Barrier element 19 is removed from layer of material 13 during use so substances 17, 18 are exposed during use. Second side 15 of layer of material 13 is connected to adhesive layer 20. Adhesive layer 20 may be any material capable of retaining layer of material 13 within retaining structure 21 including but not limited to, gel, rubber, glue. It is within the scope of this invention for layer of material 13 to not shift within retaining structure 21 of second pack 3, as the importance of at least one substance 17, 18 being in alignment with window 10 is critical to the layout of the structural components of this device. Second side 30 of layer of material 27 can have adhesive layer 34 that connects to first side 32 of removable second pack 3.

Referring again to FIGS. 3-8, second pack 3 with retaining structure 21 is connected to layer of material 13 being a medicated pad. Second pack 3 may be a hot or cold therapeutic pack having retaining structure 21 connected to first side 11 of second pack 3. Retaining structure 21 may be made of any material such as fabric, magnet, plastic, metal, and/or rubber capable of receiving a layer of material 27. Retaining structure 21 is configured to expose at least a portion of substance 17, 18 on layer of material 13 to a user's skin during use when retained by pocket 7 having window 10 of second pack 3. Layer of material 13 slides into retaining structure 21 and is held into place with flange 22. It is within the scope of this invention for first substance 17 to have an outer perimeter edge bordering substance free outer perimeter 16. This area 16 is free of substance because it is not desirable to waste substances due to cost as this area 16 will be connected to flange 22 and substantially not a user's skin. Also, substances should not come into contact with retaining structure 21 because the oils and/or medication may deteriorate the material over time. The substances 17, 18 positioned on layer of material 13, when inserted into retaining structure 21, are exposed through window 10 of pocket 7 so they can contact a user's skin during use.

It is within the scope of this invention for layer of material 13 to provide simultaneous multiple drug delivery by topical application of first substance 17 and second substance 18 retained on layer of material 13 being for example, a circular absorbent portion, in which two absorbent portions deliver different medications in close proximity. For example, first substance 17 containing menthol surrounded by second substance 18 of camphor would result in confusion of the nervous system in such a way that a higher dose of both ingredients could be applied because camphor creates the sensation of heat while menthol creates the sensation of cold, while neither is actually delivering heat or cold. By using various combinations of active ingredients of the substance in a suitable carrier emulsion, treatment of injury or discomfort can be optimized. It is within the scope of this invention for a carrier emulsion to include, but not be limited to, a combination of water, sodium lauryl sulfate, emulsifying wax, a preservative, and/or a carrier oil similar to the base emulsion used by pharmacists when making custom drugs. The base emulsion could be mixed with any substance including, but not limited to, topical anesthetics such as, Tetracaine, Lidocaine, or Benzocaine; topical antibiotics such as Bacitracin, Neomycin, or Polymyxin B; skin protectants such as, Dimethicone, Glycerin, or Aloe Vera, and/or transdermal conductors such as, Decamethylcyclopentasiloxane, Dimethyl Sulfoxide, or Dimethyl Isosorbide.

Layer of material 13 can be partially or fully saturated with at least one or a plurality of various substances 17, 18 and may be removably inserted into the therapeutic device 1 for manipulating local blood flow, to speed healing, or to reduce discomfort faster or better than traditional methods. The primary reason for using device 1 is to achieve more precise treatment than simply applying a cold or hot compress or using a cream or lotion to alleviate discomfort, thereby, improving quality of life for the user. The substances 17, 18 may be liquid saturating the layer of material 13, a gel, and/or a cream.

It is within the scope of this invention for layer of material 13 to provide simultaneous multiple herbal and/or homeopathic topical delivery to a user. The delivery of two different substances 17, 18 including, but not being limited to, an herbal, a homeopathic, and/or essential oil-type product being retained on layer of material 13 can also be extended to non-drug applications. These substances include, but are not limited to, cooling essential oils such as Eucalyptus, Peppermint, or Melaleuca; calming essential oils such as, Cardamom, Chamomile, Calendula; toxin extraction such as, Bentonite, Magnesium Sulfate, or Micronized Carbon; and/or blood flow increasing resins such as, Arnica, Capsicum, Pepper Derivatives. For example, first substance 17 may include Eucalyptus Essential Oil and second substance 18 may include Capsicum Oleoresin in a carrier oil. This application would also confuse the nervous system in such a way that it would tolerate higher doses of each ingredient which would not be tolerated if applied separately. It is within the scope of this invention for substances 17, 18 to be in close proximity of each other to allow a user to more precisely deliver treatment, to reduce healing time, and to improve quality of life. In particular, the close proximity is achieved when the first substance 17 borders the outer perimeter edge of second substance 18.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

The invention claimed is:

1. A simultaneous thermal and cooling therapeutic device, comprising:
   a first removable pack having a first temperature;
   a second removable pack having a second temperature;
   a flexible receptacle, said flexible receptacle having a first compartment, said flexible receptacle having an outer wall surface;
   said first compartment of said flexible receptacle is configured to receive said first removable pack; and,
   a pocket, said pocket is connected to said outer wall surface of said flexible receptacle;
   said pocket forming a second compartment of said flexible receptacle, said second compartment of said flexible receptacle is configured to receive said second removable pack through a first opening of said pocket;
   said pocket having a second opening forming a window and a magnetic frame bordering said window;
   said second removable pack having a first side located opposite a second side, a layer of material being removably connected to said first side of said second removable pack,
   said layer of material having a first side located opposite a second side, said layer of material having a substance-free outer perimeter,
   said layer of material having a first substance having an outer perimeter edge located in close proximity to a second substance having an outer perimeter edge, whereby, said first substance borders said outer perimeter edge of said second substance, said outer perimeter edge of said first substance borders said substance-free outer perimeter of said layer of material;
   said first side of said second removable pack having a retaining structure configured to retain at least a portion of said layer of material, said retaining structure comprising a U-shaped wall having a flange, said flange overlaying at least a portion of said substance-free outer perimeter of said layer of material, whereby, said first substance and said second substance are in alignment with said second opening of said pocket of said flexible receptacle when said flange is connected to said substance-free outer perimeter of said layer of material,
   said flange of said retaining structure of said second removable pack is made of a magnetic material, said flange of said retaining structure of said second removable pack is magnetically connected to said magnetic frame when said second pack is installed in said pocket.

2. The simultaneous thermal and cooling therapeutic device of claim 1, further comprising said pocket is made of a thermal material.

3. A simultaneous thermal and cooling therapeutic device, comprising:
- a first removable pack having a first temperature;
- a second removable pack having a second temperature;
- a flexible receptacle, said flexible receptacle having a first compartment, said flexible receptacle having an outer wall surface;
- said first compartment of said flexible receptacle is configured to receive said first removable pack; and
- a pocket, said pocket is connected to said outer wall surface of said flexible receptacle;
- said pocket forming a second compartment of said flexible receptacle, said second compartment of said flexible receptacle is configured to receive said second removable pack through a first opening of said pocket;
- said pocket having a second opening forming a window;
- said removable second pack having a first side located opposite a second side, a layer of material being removably connected to said first side of said removable second pack, said layer of material having a first side located opposite a second side, said layer of material having a substance-free outer perimeter, said layer of material having a first substance having an outer perimeter edge located in close proximity to a second substance having an outer perimeter edge, whereby, said first substance borders said outer perimeter edge of said second substance, said outer perimeter edge of said first substance borders said substance-free outer perimeter of said layer of material;
- said first side of said removable second pack having a retaining structure configured to retain at least a portion of said layer of material, said retaining structure comprising a U-shaped wall having a flange, said flange overlaying at least a portion of said substance-free outer perimeter of said layer of material, whereby, said first substance and said second substance are in alignment with said window of said pocket of said flexible receptacle when said flange is connected to said substance-free outer perimeter of said layer of material;
- said first side of said layer of material having a removable barrier element, said second side of said layer of material having an adhesive, said adhesive is configured to connect said layer of material to said first side of said removable second pack.

4. The simultaneous thermal and cooling therapeutic device of claim 1, further comprising at least one substance is a topical anesthetic.

5. The simultaneous thermal and cooling therapeutic device of claim 1, further comprising at least one substance is a topical antibiotic.

6. The simultaneous thermal and cooling therapeutic device of claim 1, further comprising said first substance being Eucalyptus Essential Oil and said second substance being Capsicum Oleoresin in a carrier oil.

* * * * *